United States Patent
Logan et al.

(10) Patent No.: US 7,160,989 B2
(45) Date of Patent: Jan. 9, 2007

(54) ANTIBODIES THAT RECOGNIZE AND BIND PHOSPHORYLATED HUMAN ANDROGEN RECEPTOR AND METHODS OF USING SAME

(75) Inventors: Susan K. Logan, New York, NY (US); Michael J. Garabedian, New York, NY (US)

(73) Assignee: New York University, New York, NY (US)

( * ) Notice: Subject to any disclaimer, the term of this patent is extended or adjusted under 35 U.S.C. 154(b) by 78 days.

(21) Appl. No.: 10/849,545

(22) Filed: May 20, 2004

(65) Prior Publication Data

US 2005/0164314 A1 Jul. 28, 2005

Related U.S. Application Data

(60) Provisional application No. 60/474,211, filed on May 30, 2003.

(51) Int. Cl.
*C07K 16/00* (2006.01)
(52) U.S. Cl. .............................. 530/388.22; 530/387.9; 530/388.1; 424/139.1; 424/143.1

(58) Field of Classification Search ..................... None
See application file for complete search history.

(56) References Cited

OTHER PUBLICATIONS

PhosphoProtein Purification Handbook, Qiagen, Dec. 2002, 24 pages.*
Reilein et al., "Regulation of organelle movement in melanophores by protein kinase A (PKA), protein kinase C (PKC), and protein phosphatase 2A (PP2A)" 1998, J Cell Biol. 142:803-813.*
Zymed Laboratories product description for catalog No. 61-8100, rabbit anti-phosphoserine, dated Apr. 6, 2005, two pages.*

* cited by examiner

*Primary Examiner*—Christina Chan
*Assistant Examiner*—Michael Szperka
(74) *Attorney, Agent, or Firm*—Browdy and Neimark, PLLC

(57) ABSTRACT

A phosphorylation site-specific antibody that recognizes phosphorylated serine 213 within the N-terminus of the androgen receptor was obtained which can be used in methods for determining the presence of activated androgen receptors in cells or tissue of human androgen responsive tissue and for screening for an androgen inhibitor or an androgen agonist.

3 Claims, 9 Drawing Sheets

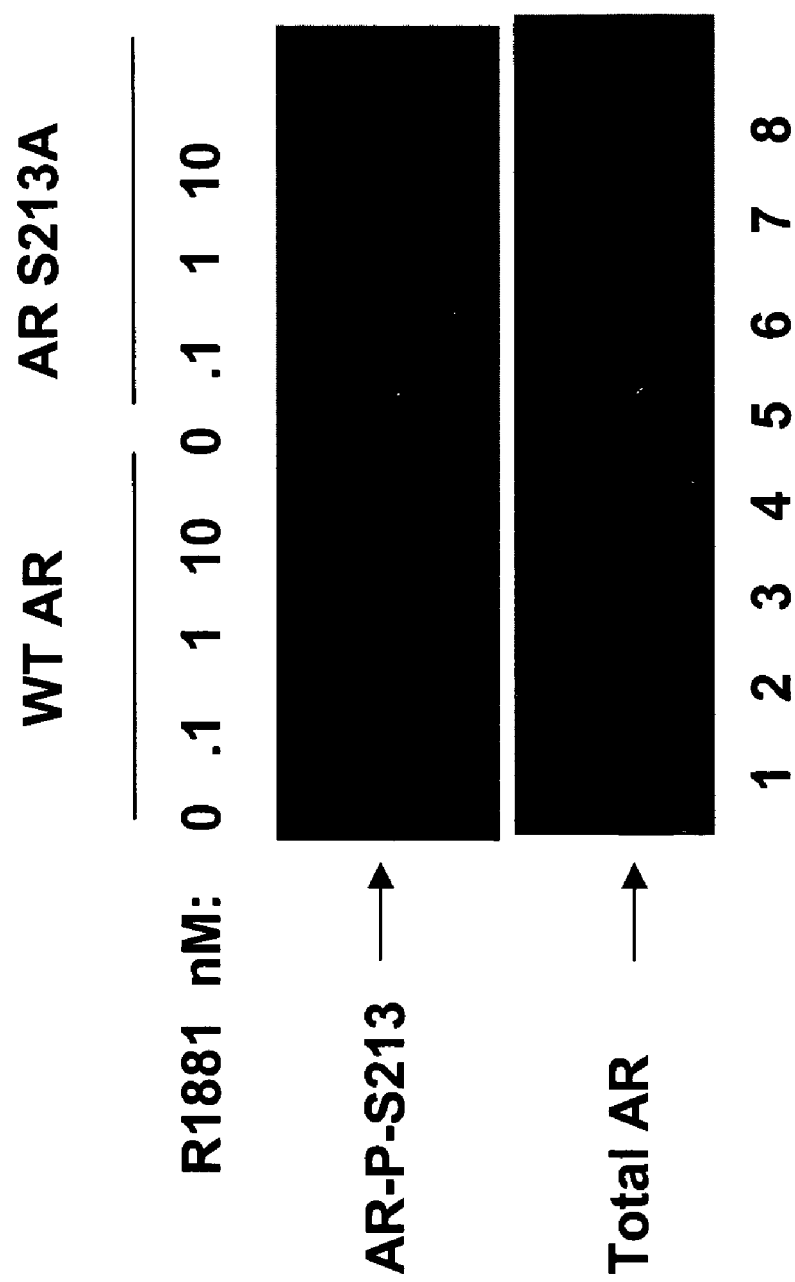

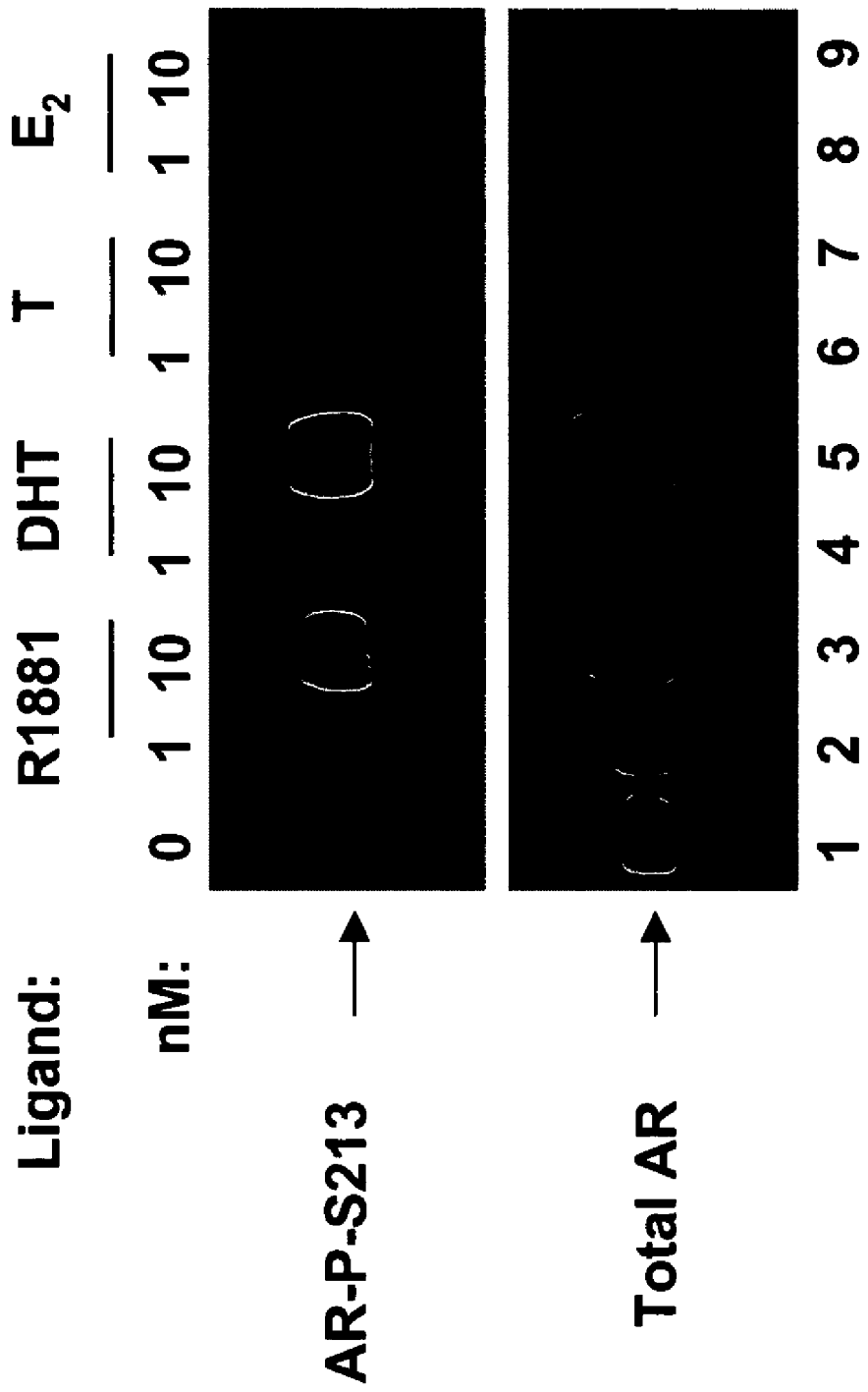

| | | | | | |
|---|---|---|---|---|---|
| AR WT | + | + | + | + | − |
| AR 213A | − | − | − | − | + |
| R1881 | + | − | + | + | + |
| LY | − | + | + | − | − |
AR-P-S213
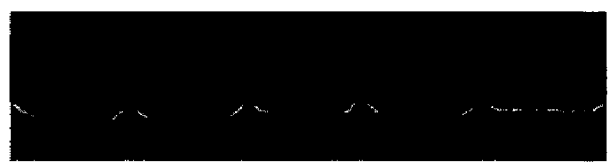
Total AR
P-Akt
2 hrs. R1881    24 hrs. R1881
1  2  3  4  5
Fig. 4A

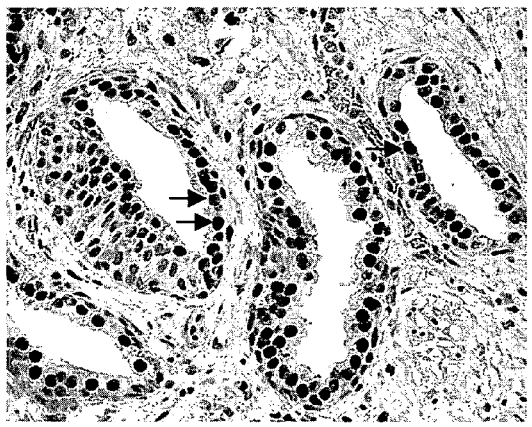 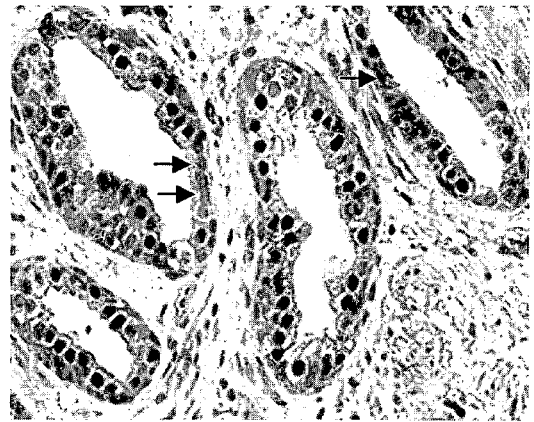
Fig. 5A                    Fig. 5B

Fig. 6A  Fig. 6B  Fig. 6C
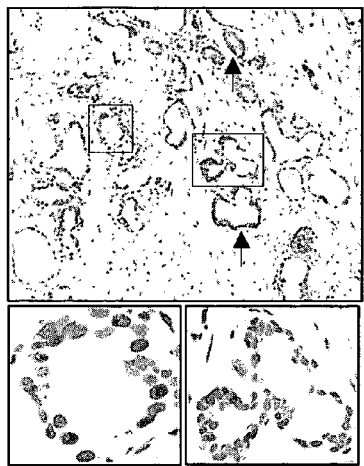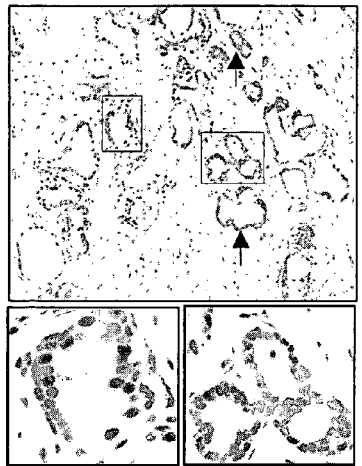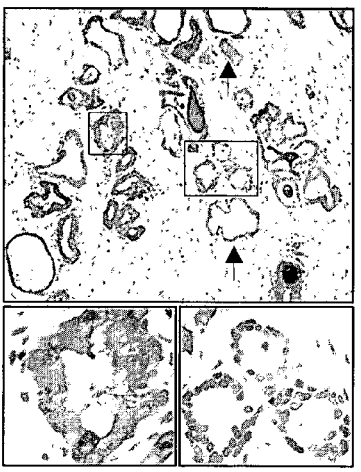
Fig. 6D  Fig. 6E  Fig. 6F  Fig. 6G  Fig. 6I  Fig. 6J

ANTIBODIES THAT RECOGNIZE AND BIND PHOSPHORYLATED HUMAN ANDROGEN RECEPTOR AND METHODS OF USING SAME

CROSS-REFERENCE TO RELATED APPLICATIONS

The present application claims priority under 35 U.S.C. §119(e) from U.S. provisional application No. 60/474,211, filed May 30, 2003, the entire content of which is hereby incorporated by reference.

GOVERNMENT LICENSE RIGHTS

The experiments performed in this application were supported in part by the National Institutes of Health, grant no. DK58024-01. The U.S. government has a paid-up license in this invention and the right in limited circumstances to require the patent owner to license others on reasonable terms as provided for by the terms of grant no. DK58024-01 awarded by the National Institutes of Health.

BACKGROUND OF THE INVENTION

1. Field of the Invention

The present invention relates to antibodies specific for epitopes of human androgen receptor in which a serine residue is phosphorylated. The present invention also relates to a method for determining the presence of activated androgen receptors and to methods for screening an androgen agonist or antagonist/inhibitor.

2. Description of the Related Art

The androgen receptor (AR) is a member of the steroid receptor (SR) family of transcriptional regulatory proteins that transduces the signaling information conveyed by androgens (Chang et al., 1995 and Wilson et al., 1991). Androgen steroid hormones direct the genetic program dictating male development. Upon androgen binding, the androgen receptor is released from the repressive effects of an Hsp90-based regulatory complex, allowing the receptor to either activate or inhibit transcription of target genes in a hormone-dependent manner (Suina et al., 1996; Fang et al., 1996; Fang et al., 1998; Picard et al., 1990; Segnitz et al., 1997; Jenster et al., 1991; and Jenster et al., 1992). In addition to the role the androgen receptor plays in male sex determination, activation of the receptor also mediates normal prostate development and malignant growth by regulating genes involved in cellular proliferation (Brinkmann et al., 1992; Dorkin et al., 1997; Hakimi et al., 1996; Trapman et al., 1996 and Jenster et al., 1999). For example, activation of the androgen receptor is not only responsible for male sexual development, it also plays a critical role in the development and progression of benign prostate hyperplasia, prostate cancer, and hair loss. The androgen receptor controls gene expression through binding with critical transcriptional regulatory proteins (coactivators and corepressors) that, in turn, allow the androgen receptor to "switch on" or "switch off" genes important for malignant prostate cell growth, benign prostate hyperplasia, and androgen-dependent hair loss.

The mechanisms underlying the specificity of AR regulation of gene expression remain enigmatic, however. Functional mapping of the androgen receptor shows that several protein regions are required for transcriptional activation (Jenster et al., 1995 and Chamberlain et al., 1996). These regions include a carboxyl-terminal domain called AF-2, as well as two regions which map to the N-terminus called AF-1a and AF-1b (FIG. 1). Recent evidence suggests that the AR cell- and promoter-specific transcriptional response is generated through interactions with regulatory proteins termed coactivators and corepressors with AF-1 and AF-2 (Cleujens et al., 1997 and Scheller et al., 1998; Chamberlain et al., 1996; Hsiao et al., 1999; Kang et al., 1999; Moilanen et al., 1998; Muller et al., 2000; Aarnisalo et al., 1998; Fronsdal et al., 1998; Fujimoto et al., 1999 and Heinlein et al., 1999).

Agonist binding to the AR C-terminal ligand binding domain promotes a conformational change and the formation of a surface for protein-protein contacts between AF-2 and additional transcriptional regulatory factors, which in turn, modulate the transcriptional activity of target genes (Glass et al., 2000 and Westin et al., 2000). Like other steroid hormone receptors, the AR is phosphorylated upon ligand binding, although the function of this phosphorylation is not well understood. The identified sites of phosphorylation within the AR include serines 16, 81, 94, 256, 308, 424, 650 (Zhou et al., 1995; Zhu et al., 2001 and Gioeli et al., 2002). Recent reports indicate that AR and the serine/threonine cytoplasmic kinase, Akt, physically interact, resulting in effects on AR-mediated transcription, AR stability and cell survival. Sequence analysis of AR indicates that it possesses two consensus Akt phosphorylation sites RXRXXS/T (SEQ ID NO:3), one located within the amino terminal domain and one within the carboxyl terminal domain. The residues, serine 213 and serine 791 have been identified as sites phosphorylated by kinase, Akt (Wen et al., 2000; Lin et al., 2001 and Lin et al., 2002).

At present, androgen receptor activity can only be altered by removing the hormone, testosterone, or by surgical or pharmacological means. Unfortunately, this approach is often short-lived, with androgen-expressing cells learning to grow in the absence of testosterone. Once this has occurred, there is no effective treatment for androgen-dependent afflictions.

Although it is well established that the AR plays a fundamental role in prostate cancer, detection of total AR levels in individual patient samples has not been predictive in determining which patients are at risk for rapid disease progression. While commercially available AR antibodies have allowed investigators to examine AR protein expression in the prostate, it is not clear whether or not the detected androgen receptor is active/ligand bound.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a molecule comprising the antigen binding portion of an antibody specific for human androgen receptor (AR) phosphorylated at residue Ser213, which molecule is preferably an antibody.

The present invention also provides a method for determining the presence of activated androgen receptors in cells or tissue obtained from human androgen responsive tissue. Detection of binding of a molecule containing the antigen binding portion of an antibody specific for human AR phosphorylated at residue Ser213 to cells or tissue treated with androgen or an androgen agonist, or to cell extracts of such treated cells or tissue, provides a determination of the presence of activated human AR in cells or tissue from androgen responsive tissue of an individual.

Further provided by the present invention is a method for determining the extent of androgen receptor suppression in prostate cancer patients treated with an androgen inhibitor as part of anti-androgen therapy. This method detects the binding of a molecule containing the antigen binding portion of an antibody specific for human AR phosphorylated at residue Ser213 to a sample of prostate cells or tissue to determine the extent of androgen receptor suppression in prostate cancer patients treated with an androgen inhibitor.

The present invention still further provides a method of screening for an androgen agonist by testing potential androgen agonists for the ability to activate human androgen receptor, where activation is determined by detecting binding of a molecule containing the antigen binding portion of an antibody specific for human AR phosphorylated at residue Ser213 to androgen responsive cells treated with a potential androgen agonist, or to an extract of such treated cells or tissue.

Likewise, a method of screening for an androgen inhibitor/antagonist by testing potential androgen inhibitors for the ability to suppress the activation of human androgen receptors in androgen responsive cells or tissue in the presence of androgen or androgen agonist is also further provided by the present invention.

BRIEF DESCRIPTION OF THE DRAWINGS

FIGS. 2A–2D are Western blots showing that AR-P-S213 antibody recognizes wild type but not mutant S213A AR. In FIG. 2A, wild type or S213A AR constructs were transfected into 293 cells, which were treated or untreated with the AR ligand R1881. Cell lysates were subjected to Western blot analysis and incubated with either antibody against AR-P-S213 (top) or antibody against total AR protein (bottom). The results indicate that the antibody against AR-P-S213 recognizes ligand-bound wild type AR, but not S213A mutant AR. In FIG. 2B, wild type AR was transfected into HEK 293 cells and treated for 1 hour with the AR agonist, R1881(10 mM), antagonists Casodex (Cdx) or Flutamide (Flu) at 10 μM or with both agonist and antagonist (Cdx+R1881; Flu+R1881). Cell lysates were subjected to immunoblot analysis with AR-P-213 or total AR antibody. The results indicate that antagonists do not cause S213 phosphorylation, but are functional since they can diminish S213 phosphorylation when added to the cells along with R1881 (Cdx+R1881 and Flu+R1881). In FIG. 2C, HEK 293 cells were transfected with wild type AR or with the AR serine 213 to alanine mutant. The cells were treated with 0.1, 1 or 10 nM R1881 and cell lysates were subjected to immunoblot analysis with AR-P-213 or total AR antibody. Wild type AR shows robust phosphorylation at 10 nM R1881, but not at lower levels. As expected, the AR S213A mutant does not show phosphorylation. In FIG. 2D, HEK 293 cells were transfected with wild type AR and treated with 1 or 10 nM R1881, di-hydrotestosterone (DHT), testosterone (T) or estrogen ($E_2$). As expected, estrogen treatment does not result in AR phosphorylation, testosterone results in weak phosphorylation, while DHT and R1881 cause robust AR phosphorylation.

FIG. 3A shows Western blot analysis of 293 cells transfected with HA-AR and treated for 5 min (5), 10 min (10), 20 min (20), 40 min (40), 60 min (60) or 24 hours of the synthetic androgen ligand (agonist), R1881. Top panel is blotted with P-S213 (AR-P-S213), and the bottom panel is blotted with an antibody against total cellular AR (#441, Santa Cruz). FIG. 3B shows Western blot analysis of cytoplasmic (cyto) or nuclear (nucl) lysates made from 293 cells transfected with either wild type AR (AR wt) or the AR S213A mutant and treated with R1881. The results indicate that P-S213 AR is predominantly nuclear, while total AR is present in both the cytoplasmic and nuclear fractions.

FIGS. 4A and 4B are Western blots of kinase phosphorylation of AR-P-S213. In FIG. 4A, HEK 293 cells were transfected with WT AR or AR S213A and pre-treated with LY for 15 minutes where indicated followed by stimulation with R1881 for 2 hours (lanes 1–14) or 24 hours (lanes 4 and 5). Cell lysates were then immunoblotted with antibody against AR-P-S213 (top panel), total AR (middle panel) or phospho-Akt serine 473 (lower panel). FIG. 4B shows that IGF-1 treatment alone does not result in AR phosphorylation in the absence of R1881. 293 cells were transfected as above and treated with IGF-1 alone for 5 or 10 minutes (m) or for 2 hours (h, lanes 1–4) or with R1881 alone (lane 5) or R1881 and IGF-1 (lanes 6 and 7). Cell lysates were made and subjected to immunoblot analysis using antibodies against AR-P-S213, total AR, phospho-MAPK (P-MAPK), total MAPK, Akt P-473 (P-Akt) or total Akt. While MAPK is phosphorylated in response to IGF-1, activation of MAPK does not correlate with AR S213 phosphorylation. Akt is constitutively active in these experiments under all conditions and therefore could play a role in AR phosphorylation.

FIGS. 5A and 5B show immunohistochemical staining of human archival prostate tissue sections incubated with either antibody against total AR protein (FIG. 5A) or antibody against AR phospho-S213 (FIG. 5B). Positive reactivity is indicated by the dark stain. Antibody against total AR stains nuclei (dark spots) of epithelial and stromal cells, antibody against AR-P-S213 stains nuclei (dark spots) of epithelial cells only. Arrows indicate cells that are positive for AR, but not for AR-P-S213.

FIGS. 6A–6G and 6I-6J (there is no FIG. 6H) show immunohistochemistry performed in prostate cancer tissue sections incubated with antibody against total AR (FIGS. 6A,D,E) AR-P-S213 (FIGS. 6B,F,G) and PSA (FIGS. 6C,I, J). In the larger photographs (FIGS. 6A–C), the small boxed region on the right outlines prostate glands that stain negatively for PSA, while the small boxed region on the left shows a gland that stains positively for PSA. Arrows in FIGS. 6A–C indicate additional glands that stain negatively for PSA. Each boxed region is shown at higher magnification below the panel from which it was taken. All sections that stain positively for PSA, stain positively for AR and P-AR (FIGS. 6D,F,I). Regions that stain negatively for PSA (FIG. 6J), stain moderately for AR (FIG. 6E) and show no nuclear staining and some weak cytoplasmic staining of AR-P-S213 (FIG. 6G).

Figure 1:
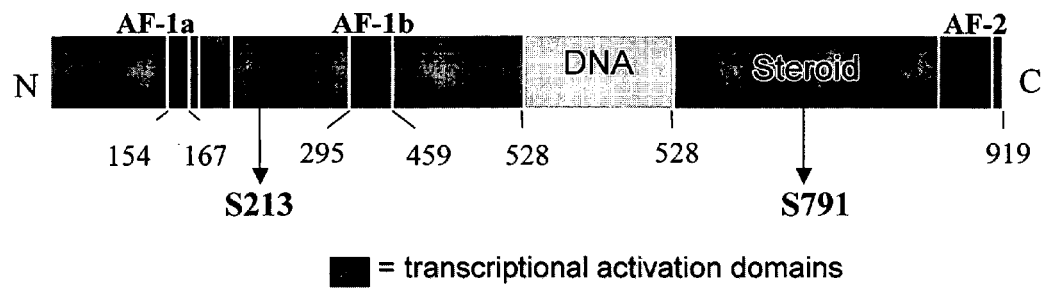
FIG. 1 schematically shows the structure of human androgen receptor (AR) functional domains and the location of phosphorylated serine residues S213 and S791. The DNA binding domain (DNA), ligand binding domain (steroid), poly-glutamine region (Q), and activation function domains (AF-1 and AF-2) are indicated. The two sites of putative Akt phosphorylation, S213 and S791, are indicated by arrows.

The lumen of the urethra is indicated for orientation (U). Tissue samples are incubated with either AR-P-S213 antibody (FIGS. 7A, C, E and G) or total AR antibody (FIGS. 7B,D,F and H). Specimens are shown at both 200×(FIGS. 7A,B,E and F) and 400x (FIGS. 7C,D,G and H) magnification. At 14 weeks, AR-P-S213 is detected in nuclei of epithelial cells adjacent to the lumen of the urethra but not in the surrounding stroma (str) (FIGS. 7A and C), whereas total AR is present in the nuclei of all prostate cell types (FIGS. 7B and D). At 24 weeks, AR-P-S213 is undetectable (FIGS. 7E and G) whereas total AR is clearly present in both stromal and epithelial cells (FIGS. 7F and H).

DETAILED DESCRIPTION OF THE INVENTION

Since phosphorylation increases upon ligand binding to the receptor, the present inventors believed that antibodies made against phosphorylation sites within the receptor should recognize the active (ligand-bound) form of the receptor. An object of the present invention is to make an antibody that recognize activated androgen receptor (AR) for use as a diagnostic in evaluating the potential aggressiveness of prostate cancers. Thus, androgen hormone-dependent phosphorylation is a surrogate marker for activated AR in vivo. The rationale for focusing on the AR is that AR signaling regulates prostate cell growth to the extent that blocking AR function is a mainstay of prostate cancer treatment. However, the ability to monitor the activated, hormone-bound AR or the suppression thereof in patients undergoing androgen blockade therapy cannot be determined. Progress in this regard has been hindered by the lack of a simple assay to detect receptor phosphorylation in vivo.

To develop a reagent that would recognize the active form of the androgen receptor, the present inventors have generated a phosphorylation site-specific antibody that recognizes S213 within the N-terminus of AR. This site was chosen because it has recently been suggested that Akt, a cytoplasmic protein kinase and a downstream target of PI 3-kinase, phosphorylates the AR at serines 213 (S213) and 791 (S791)(Wen et al., 2000; Lin et al., 2001–2002). Akt is a serine/threonine kinase known to be important in cell survival and has been shown to be amplified or over-expressed in tumors (Bellacosa e a., 1995; Nakatani et al., 1999).

The sequence of the human androgen receptor (SEQ ID NO:4), to which the numbering of the serine residue positions refer, is presented in the NCBI GenBank database under accession no. M20132 (GI:178627), citing Lubahn et al. (1988).

The laboratories of the present inventors have produced antibodies that specifically recognize the phosphorylated form of human AR at serine residue 213 (S213) of SEQ ID NO:4 and found that the transcriptional activity of AR correlates with the amount of phosphorylation at S213, suggesting that S213 phosphorylation is an important biomarker for activated AR in vivo. This is the first time that phosphorylation site-specific antibodies have been produced against AR, and the AR-P-S213 antibody represents a means for identifying whether AR is active or not in vivo. Thus, the present invention provides an antibody, and more generally, a molecule containing the antigen binding portion of an antibody specific for androgen receptor phosphorylated at residue S213.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')2 fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked VH-VL or single-chain FV). Both VH and VL may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the VH and VL chains are known, may be accomplished in accordance with the methods described, for example, in U.S. Pat. Nos. 4,946,778, 5,091,513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be readily obtained by methods known to those skilled in the art. See, for example Kohler et al, (1975); U.S. Pat. No. 4,376,110; Harlow et al, (1988); and Colligan et al, (1994–2003), the entire contents of which references are incorporated entirely herein by reference. Such antibodies may be of any immunoglobulin class including IgG, IgM, IgE, IgA, and any subclass thereof. The hybridoma producing the mabs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al (1984), Morrison et al (1984), Boulianne et al (1984), European Patent 0 125 023 (1984), Neuberger et al (1985), European Patent 0 171 496 (1985), European Patent 0 173 494 (1986), WO 8601533 (1986), European Patent 0 184 187 (1986), Sahagan et al (1986); WO 9702671 (1987), Liu et al (1987), Sun et al (1987), Better et al (1988), and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')2 fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

Anti-androgen (androgen blockade) therapy is used widely in clinical medicine as the primary means of treating prostate cancer. Unfortunately, most prostate cancers eventually become resistant to anti-androgen therapy. The molecule of the present invention, i.e., the phospho-AR antibody against the S213, will allow monitoring of the response to anti-androgen therapy by assaying AR phosphorylation at S213 in prostate cells or tissues to determine if anti-androgen therapy is working as expected in individual patients and to pinpoint patients that will rapidly develop androgen-independent disease. For example, paraffin embedded tissue samples from core biopsies or radical prostatectomy can be analyzed immunohistochemically using the antibody/molecule of the present invention. Thus, the present invention provides a method for determining the extent of androgen suppression in prostate cancer patients treated with an androgen inhibitor as anti-androgen therapy. This method involves reacting a sample of prostate cells or tissue from a prostate cancer patient with an antibody/molecule of the present invention and then detecting binding of the antibody/molecule to the sample of prostate cells or tissue to determine the presence of activated androgen receptors in the sample and thereby to determine the extent of androgen receptor suppression in prostate cancer patients treated with an androgen inhibitor.

The present invention also provides a method for determining the presence of activated androgen receptors in cells obtained from human androgen responsive tissue using the AR phosphorylation-site specific antibody/molecule of the present invention. This method can be in vitro or in vivo and involves treating cells or tissue from androgen responsive human tissue of an individual with an androgen or androgen agonist, reacting a sample of the treated cells or tissue, or a cell extract thereof, with the antibody/molecule of the present invention, and then detecting binding of the antibody/molecule to the treated cells or tissue, or a cell extract thereof, to determine the presence of activated androgen receptors in cells from androgen responsive human tissue of the individual, such as the prostate.

When androgen or androgen agonist in the treating step is administered in vivo to an individual, then a sample of treated cells or tissue from androgen responsive human tissue of the same individual is removed from the individual before reacting the sample with the antibody or molecule of the present invention. Otherwise, the cells or tissue of androgen responsive human tissue of an individual can be treated in vitro with androgen or androgen agonist.

While generally most tissues in humans are considered androgen responsive because they all have androgen receptors, there is variation in the degree of responsiveness. Examples of androgen responsive human tissue include thyroid, prostate, breast, muscle, spinal, lung, and liver. Other suitable sources of cells from androgen responsive human tissue can be readily ascertained by the degree of androgen responsiveness in general. For instance, there is evidence that androgens inhibit breast cancer growth although the mechanism is poorly understood. Immunohistochemistry done on breast cancer tissue samples using the antibody may provide some insight into this problem and may also be predictive of clinical outcome. Androgens also play a role in secondary sex characteristics such as male pattern baldness and muscle mass. The antibody or molecule of the present invention may be useful in development of treatments for baldness and muscle wasting. Androgen Insensitivity Syndrome is a condition whereby mutations in the androgen receptor render the individual unable to respond to androgens and result in people that have a Y chromosome (genotypically male but appear to be female). There are conditions in individuals having partial androgen insensitivity syndrome where the antibody or molecule of the present invention may be useful for diagnosis and treatment prescription. Spinal and bulbar muscular atrophy, also called Kennedy's disease, is an adult onset neurodegenerative disease that is thought to occur due to an increase in polyglutamine repeats in the N-terminus of the AR. Since this disease is associated with decreased levels of AR activity, the antibody or molecule of the present invention may be useful for diagnosis of this disease as well.

The present invention further provides a method of screening for an androgen inhibitor such as from a library of potential candidates. The method involves incubating human androgen responsive cells or tissue having androgen receptors in the presence of androgen or androgen agonist and in the presence or absence of a potential androgen inhibitor and then reacting the incubated cells or tissue, or a cell extract thereof, with the antibody or molecule of the present invention. Afterwards, the level of binding of the antibody or molecule of the present invention to the incubated cells or tissue, or to a cell extract thereof, is detected, and based on the detected level of binding, identifying a potential androgen inhibitor as a androgen inhibitor if the level of suppression of androgen receptor activation in androgen responsive cells or tissue in the presence of the potential androgen inhibitor is substantially greater than in the absence of the potential androgen inhibitor.

Likewise, the present invention provides a method of screening for an androgen agonist, such as also from a library of potential candidates. The method involves incubating human androgen responsive cells or tissue having androgen receptors in the presence or in the absence of a potential androgen agonist that activates androgen receptors and then reacting the incubated cells or tissue, or a cell extract thereof, with the antibody or molecule of the present invention. Afterwards, the level of binding of the antibody or molecule of the present invention to the incubated cells or tissue, or to a cell extract thereof, is detected and based on the detected level of binding, identifying a potential androgen agonist as a androgen agonist if the level of activation of androgen receptors in androgen responsive cells or tissue in the presence of the potential androgen agonist is substantially greater than in the absence of the potential androgen agonist.

The term "substantially greater" or "substantially more" as used herein is intended to mean a level of activation or suppression of androgen receptors in the presence of a potential androgen agonist or androgen inhibitor, respectively, at least about two times that of the basal level in the absence of the potential androgen agonist or androgen inhibitor. As the sensitivity of detection using the antibody or molecule of the present invention is quite good, even if the basal level of activation or suppression is very low, a two fold increase is detectable.

The screening methods described above can also be used to screen for partial agonists or antagonists or for selective androgen responsive modulators (SARMs), which may allow development of non-hormone agents that have some desirable properties of the hormone but without some of the undesirable effects, e.g., improving bone strength in women without the undesirable side effect of growth mustaches. It may be necessary to perform the screening methods of the present invention on more than one androgen responsive tissue, i.e., a panel of androgen responsive tissue, to determine selectivity of any potential candidate.

Androgen inhibitors and agonists identified by the above methods of the present invention are also intended to encompassed by the present invention.

Having now generally described the invention, the same will be more readily understood through reference to the following example which is provided by way of illustration and is not intended to be limiting of the present invention.

EXAMPLE

Characterization of the AR-P-S213 antibody has shown that it specifically recognizes phosphorylated serine 213 in an agonist-dependent fashion. The phosphorylation takes place with rapid kinetics and is inhibited by the PI3K inhibitor, LY294002. The bulk of the phosphorylated species is found in the nucleus as shown by immunoprecipitation of nuclear and cytoplasmic extracts. In vivo analysis of AR-P-S213 indicates that the antibody reacts with antigen in prostate tissue and in human fetal tissue. In adult prostate tissue, AR-P-S213 antibody specifically stains prostate epithelial cells that are positive, for PSA protein expression. This suggests that AR-P-S213 recognizes AR in cells where it is transcriptionally active, since PSA is directly transcriptionally regulated by AR. In support of this idea, the present inventors show that in fetal tissue, AR-P-S213 antibody reacts positively with epithelial cells at a stage of development with high endogenous androgen levels, but does not react with tissue at a later stage, when endogenous androgen levels are low. Thus, AR-P-S213 recognizes ligand bound AR as assessed by both biochemical and in vivo analysis, and therefore represents a new tool to study the role of the AR in prostate cancer progression. The experimental procedures used and the experimental results obtained are presented below.

Experimental Procedure

Antibody Production: Phosphopeptides corresponding to human AR sequences $^{202}$EGSSSGRAREAS(PO$_4$)GAPTSS$^{219}$ (SEQ ID NO:1) were synthesized by Anaspec Inc. (San Jose, Calif.). The consensus sequence for Akt phosphorylation within this peptide is RAREASG (SEQ ID NO:2). A cysteine residue was added to the N terminus of each peptide to facilitate chemical cross-linking. Each phosphopeptide was coupled to keyhole limpet hemocyanin and used to immunize rabbits (Covance Research Products, Inc., Denver, Pa.). Six rabbits were immunized and the serum from each was separately tested for immunoblotting.

Immunohistochemistry: Immunohistochemistry was performed using the AR-P-S213 antibody. All human samples were used with approval of the New York University School of Medicine Institutional Review Board. Paraffin embedded tissue sections were dewaxed in xylene, rehydrated and washed in TBS, pH7.4. For antigen retrieval, paraffin sections were heated in a microwave oven (900 W) in Target Retrieval Solution (Dako), followed by treatment with 3% H$_2$O$_2$ and blocking with 20% normal goat serum. Sections were then incubated with AR-P-S213 antibody followed by incubation with a biotinylated rabbit secondary. An avidin-biotin complex was formed and developed using diaminobenzidine substrate. Slides were counter-stained with hematoxylin.

Site directed mutagenesis: The AR S213A mutant AR was made by site directed mutagenesis using a QuikChange Site-Directed Mutagenesis Kit (Stratagene, La Jolla, Calif.). The mutation was verified by DNA sequencing. Protein expression of the construct was verified by Western blot analysis using anti-AR antibody (Santa Cruz, N-20).

Cell culture and transient transfection: A human embryonic kidney cell line (293) was obtained from the American Type Culture Collection and maintained in DMEM (Invitrogen, Grand Island, N.Y.) supplemented with 10% fetal bovine serum (FBS; Hyclone Laboratories, Logan, Utah), 50 U/ml each of penicillin and streptomycin, and 2 mM L-glutamine (Invitrogen). The androgen-sensitive prostate cancer cell line (LNCaP) was maintained in RPMI-1640 (Invitrogen) supplemented with 10% fetal bovine serum (FBS; Hyclone Laboratories, Logan, Utah), 50 U/ml each of penicillin and streptomycin, and 2mM L-glutamine (Invitrogen). For transfections, 4.2×10$^6$ 293 cells were seeded into each 10 cm dish and transfected with wtAR or mutant AR S213A using Lipofectamine 2000 (Invitrogen) according to manufacturer's instructions. After 3 hours, the media was removed and replaced with phenol red-free DMEM plus 10% FBS. 18 hours later the cells were fed with fresh phenol red-free DMEM plus 10% FBS with either the synthetic androgen ligand, 10 nM R1881 (Perkin Elmer Life Sciences) or an identical volume of 100% ethanol and incubated for 12 hours. Cell lysates were then made for Western blot analysis.

Preparation of nuclear and cytoplasmic lysates: Nuclear and cytoplasmic lysates were prepared according to (Lee et al., 1988). Cells (1×10$^6$ cells) were collected by centrifugation, swelled in a hypotonic buffer, and lysed by extruding the cells through a 25-gauge hypodermic needle. This homogenate was then centrifuged at 14,000 rpm for 5 min to pellet the nuclei, and the supernatant was saved as the cytoplasmic fraction. The proteins were extracted by re-suspension of the nuclear pellet in a high salt buffer and separation of debris by centrifugation. The resulting supernatant was retained as the nuclear fraction.

Results

Figures 2A, 2B:
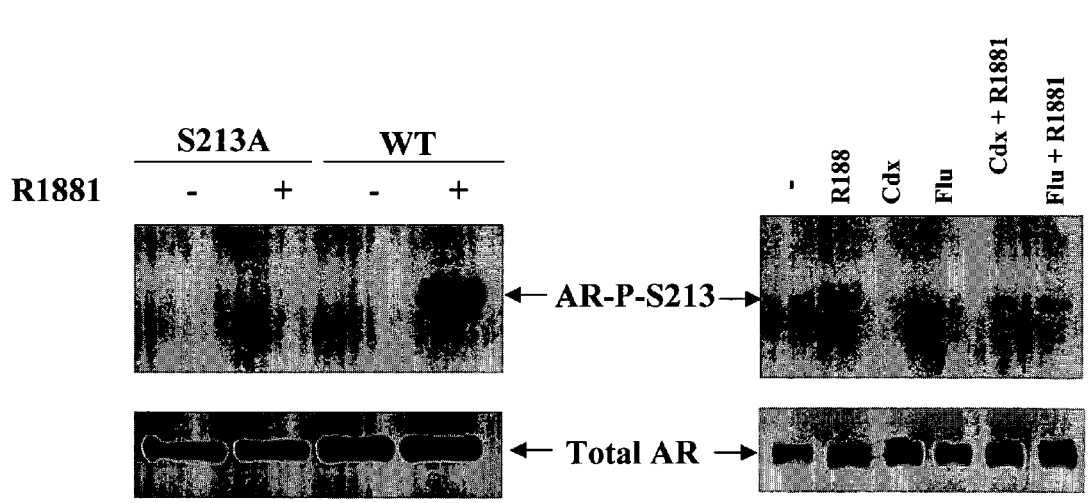

Antibodies were generated against the AR phospho-peptide $^{202}$EGSSSGRAREAS(PO$_4$)GAPTSS$^{219}$ (SEQ ID NO:1) and the anti-sera were subjected to Western blot analysis. The specificity of the antibodies is demonstrated by the fact that the antibodies recognize wild type AR but do not recognize a mutant AR containing a serine to alanine mutation at site 213 (S213A) which cannot be phosphorylated at this site (FIGS. 1 and 2A). Thus, the antibody specifically recognizes phosphorylated serine 213. Additionally, the experiment shows that phosphorylation of S213 occurs only in the presence of the synthetic androgen ligand R1881, suggesting that interaction of R1881 with the ligand binding domain in the AR C-terminus induces a conformational change in the N-terminus that reveals the AR S213 site for phosphorylation by cellular kinases.

To determine if AR S213 is phosphorylated in the presence of both AR agonists and antagonists, 293 cells overexpressing AR were treated with R1881, 5'-hydroxyflutamide (Flu), or Casodex (bicalutamide, Cdx). AR S213 is phosphorylated in the presence of the androgen agonist, R1881, but not in the presence of the antagonists, Flu or Cdx, indicating that the antibody specifically recognizes the activated (agonist bound) form of the receptor (FIG. 2B). To verify that the antagonists are functional, the present inventors show that they in fact diminish S213 phosphorylation in the presence of R1881 (FIG. 2B, Cdx+R1881 and Flu+R1881). Furthermore, wild type AR shows robust phosphorylation at 10 nM R1881 but not at lower levels (FIG. 2C). As expected, the AR S213A mutant does not show phosphorylation and, in contrast to DHT and R1881, which cause robust AR phosphorylation, estrogen does not result in AR phosphorylation and testerone results in weak phosphorylation. Therefore, the AR-P-S213 antibody is a surrogate biomarker for the activated AR in vivo and will allow the determination of the activation status of the AR during normal and malignant prostate growth.

Figure 3A:
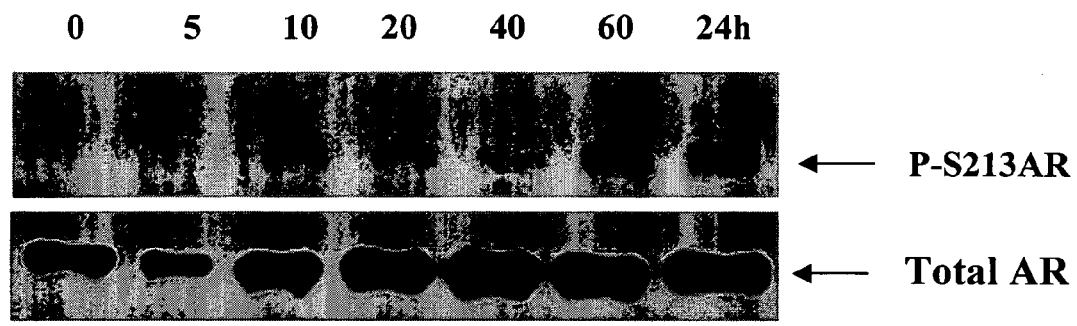
FIGS. 3A and 3B are Western blots showing the time course and sub-cellular localization of AR S213 phosphorylation.
Figure 3B:
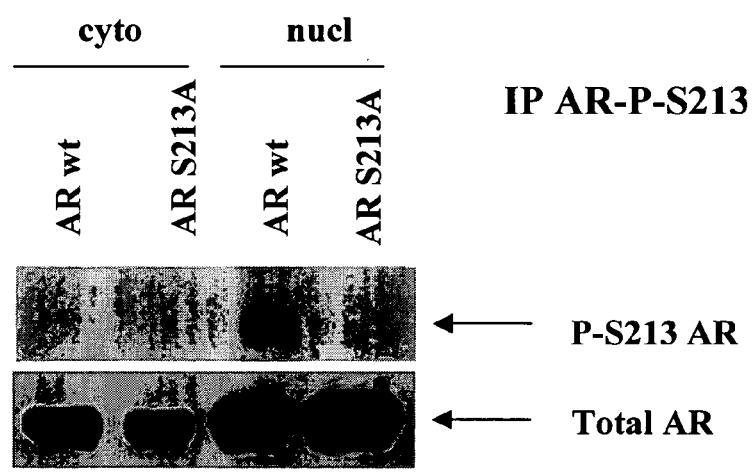

To determine the kinetics of AR phosphorylation, cells were treated with ligand for the indicated times (FIG. 3A). Phosphorylation above background is obvious at 60 minutes and may occur as early as 10 minutes (FIG. 3A). To assess the subcellular localization of AR-P-S213, fractionation studies were conducted in the presence of R1881. AR was immunoprecipitated from the nuclear and cytoplasmic extracts and then subjected to immunoblot analysis with AR-P-S213 antibody. FIG. 3B shows that, as expected, total AR is predominantly nuclear upon R1881 treatment (compare total AR panel, cytoplasmic versus nuclear fractions). Given that phosphorylation of AR S213 is ligand dependent, the bulk of AR-P-S213 is as expected, also found in the nuclear fraction.

Figure 4B:
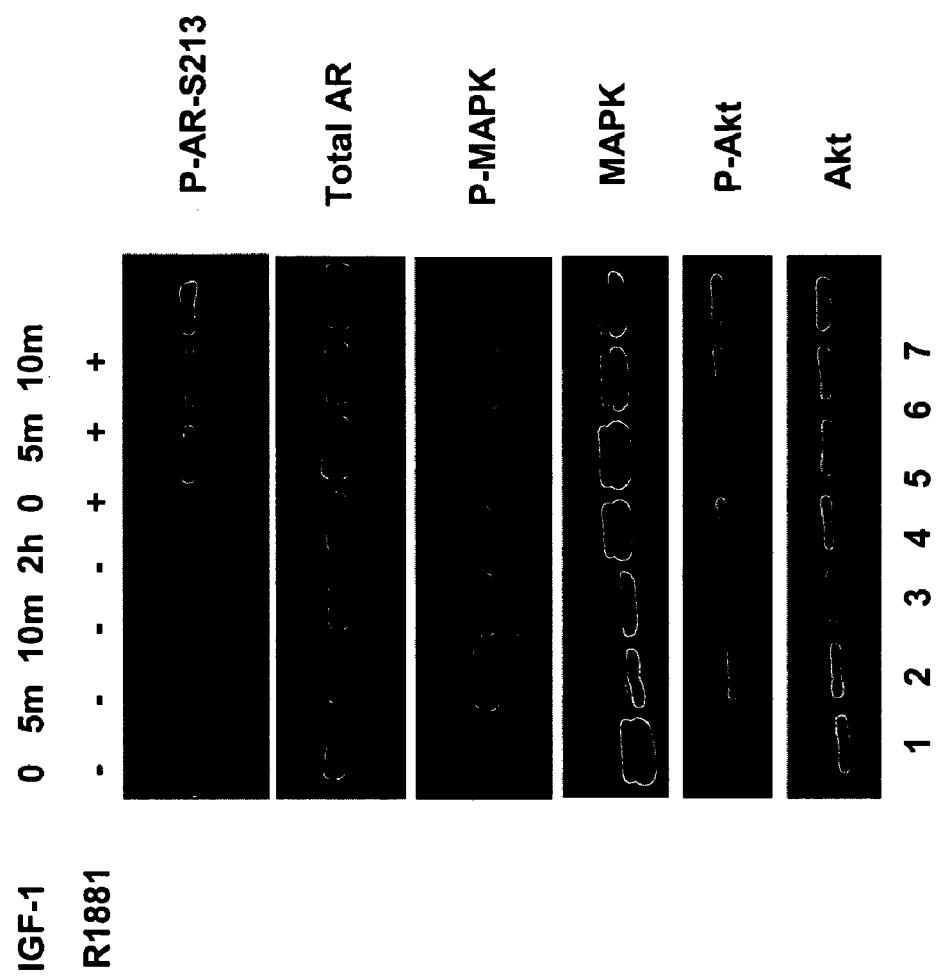

The experiments above indicate that AR is phosphorylated in the presence of ligand (R1881), but do not indicate the cellular kinase(s) that might be involved. To determine if the PI3K/Akt pathway plays a role in the in vivo phosphorylation of S213, cells were treated with R1881 in the presence or absence of the PI3K inhibitor, LY294002. The results indicate that LY294002 can inhibit AR S213 phosphorylation in cells treated with R1881 (compare the AR-P-S213 panel, FIG. 4A, lane 1 versus 3) suggesting that this pathway is instrumental in AR-S213 phosphorylation. Note that LY294002 decreases endogenous levels of Akt phosphorylation (P-Akt panel, lanes 2 and 3) while total AR levels do not change. Of course, experiments using pharmacological inhibitors must be interpreted with caution due to possible non-specific effects, and similar experiments are underway to assess the effect of dominant negative PI3K and Akt variants on AR S213 phosphorylation. FIG. 4B shows that IGF-1 treatment alone does not result in AR phosphorylation in the absence of R1881. While MAPK is phosphorylated in response to IGF-1, activation of MAPK does not correlate with AR S213 phosphorylation. Akt is constitutively active in these experiments under all conditions and therefore could play a role in AR phosphorylation.

To determine if the antibody could recognize the activated form of the receptor in prostate tissue sections, immunohistochemistry on paraffin embedded archival prostate tissue was performed using affinity purified AR-P-S213 antibody (FIG. 5A). The results indicate that AR-P-S213 antibody detects phospho-AR in a pattern that is different from that of total AR protein. While total AR protein is detected in most epithelial cells (glandular structures), the pattern of AR-P-S213 is more heterogeneous suggesting cell to cell differences in activation of AR. In addition, while total AR stains prostate stromal cells (cells between glands), AR-P-S213 does not, suggesting that there is little AR signaling in fully differentiated adult prostate stromal tissue or that different AR sites are phosphorylated in the stromal cell context. As a control for antibody specificity, tissues were incubated with the AR-P-S213 antibody and either immunizing peptide or an irrelevant peptide. There was no staining in the presence of the immunizing peptide while the presence of the irrelevant peptide had no effect on the staining pattern (not shown).

If AR-P-S213 is truly indicative of agonist bound AR in vivo, its distribution should be similar to the cell type specific expression of Prostate Specific Antigen (PSA), a gene known to be a direct transcriptional target of AR. To determine if this is the case and to analyze the expression pattern of AR-P-S213 in prostate cancer, immunohistochemistry was performed on consecutive prostate cancer tissue sections incubated with antibody that recognizes total AR, AR-P-S213 or PSA (FIGS. 6A-6J). The results indicate that AR-P-S213 correlates with cellular expression of PSA, while total AR is detected regardless of the PSA expression pattern. By these criteria, AR-P-S213 accurately reflects the activation status of AR in vivo.

To examine AR-P-S213 distribution during developmental differentiation, the present inventors assessed the pattern of AR-P-S213 protein in the region of the urogenital sinus from which the prostate develops in human fetal tissue. Prostate specimens from human fetuses 14 and 24 weeks of gestational age were obtained following surgical abortion performed for reasons unrelated to this investigation. Approval for the collection of specimens was obtained by the New York University School of Medicine Institutional Review Board. Informed consent was obtained for all specimens.

In male fetal development, testosterone secretion from the testes begins at 8 weeks of development. The serum levels remain low (<1 ng/ml) until about 11 weeks and peak between 12 and 18 weeks (approaching 5.8 ng/ml) before sharply declining again to low levels (<1 ng/ml) after 18 weeks.

Figure 7A:
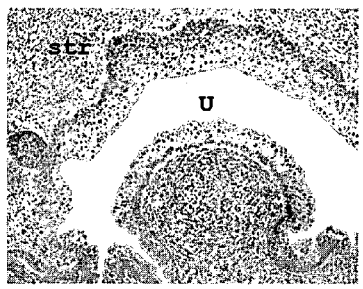
FIGS. 7A–7H show AR-P-S213 and total AR expression in human fetal prostate development in paraffin sections of 14 week old and 24 week old human fetal urogenital sinus.
Figure 7B:
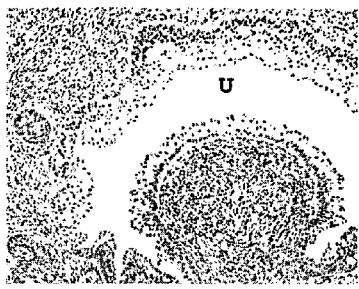
Figure 7C:
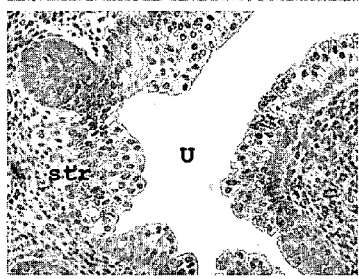
Figure 7D:
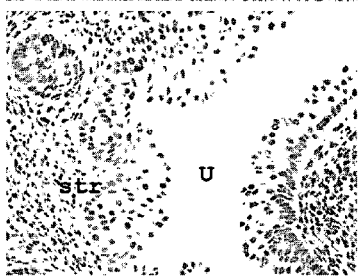
Figure 7E:
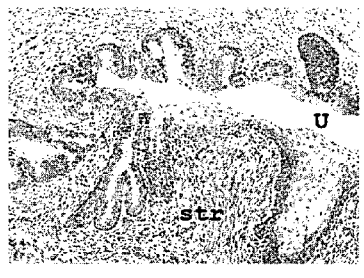
Figure 7F:
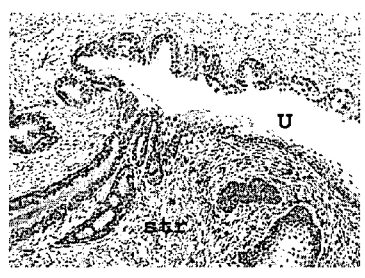
Figure 7G:
Figure 7H:
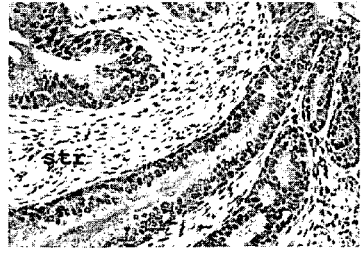

Sections through the urogenital sinus region of a 14 week-old fetus show a cell-free region in the center which is the lumen of the urethra (U, FIGS. 7A and 8B). Adjacent to the lumen, are columns of epithelial cells that are surrounded by mesenchymal or stromal tissue (str). At 14 weeks of development, staining with AR-P-S213 antibody shows phosphorylated AR protein in the layer(s) of the epithelial cells adjacent to the lumen of the urethra, but not in stromal cells (FIGS. 7A and 7C). Incubation with total AR antibody however, shows staining of both the epithelial cells surrounding the lumen, and the stromal cells (FIGS. 7B and 7D). Tissue from the urogenital region of a 24 week old fetus was also stained with AR-P-S213 antibody. Since the urethra is much larger at this point in development, only a portion of the urethra is visible in the photograph (FIGS. 7E-7H). In this case, there is little if any staining of AR-P-S213, correlating with decreased levels of endogenous androgens after 18 weeks of development (FIGS. 7E and 7G). In contrast, incubation with antibody against total AR shows strong AR expression in multiple layers of epithelial cells adjacent to the lumen of the urethra (FIGS. 7F and 7H) as well as in stromal cells. Importantly, increased AR-P-S213 expression correlates with the burst of testicular production of endogenous androgen during male development in the $12^{th}$ to $18^{th}$ week of human fetal gestation.

In addition to its role as a diagnostic, AR-P-S213 also provides an important new tool to the basic research community. It enables investigation into the mechanism of cross talk between growth factor receptor signaling pathways, which activate PI 3-kinase and Akt, and the AR signaling pathway in androgen-dependent versus independent prostate cancer. Such cross talk has been proposed to play an important role in prostate cancer metastasis.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aarnisalo, P., Palvimo, J. J., and Janne, O. A., CREB-binding protein in androgen receptor-mediated signaling, *Proc Natl Acad Sci USA*, 95(5):2122–7 (1998)

Bellacosa, A., de Feo, D., Godwin, A. K., Bell, D. W., Cheng, J. Q., Altomare, D. A., Wan, M., Dubeau, L., Scambia, G., Masciullo, V., and et al., Molecular alterations of the AKT2 oncogene in ovarian and breast carcinomas, *Int J Cancer*, 64(4), 280–5 (1995)

Better et al, "*Escherichia coli* secretion of an active chimeric antibody fragment", *Science* 240:1041–1043 (1988)

Boulianne et al, "Production of functional chimaeric mouse/human antibody", *Nature* 312:643–646 (1984)

Brinkmann et al., "The human androgen receptor: structure/function relationship in normal and pathological situations", *J Steroid Biochem Mol Biol*, 41:361–8 (1992)

Cabilly et al, "Generation of antibody activity from immunoglobulin polypeptide chains produced in *Escherichia coli*", *Proc Natl Acad Sci USA* 81:3273–3277 (1984)

Chamberlain, N. L., Whitacre, D. C., and Miesfeld, R. L., Delineation of two distinct type 1 activation functions in the androgen receptor amino-terminal domain, *J Biol Chem*, 271(43):26772–8 (1996)

Chang et al., "Androgen receptor: an overview", *Crit Rev Eukaryot Gene Expr*, 5:97–125 (1995)

Cleutjens, C. B., Steketee, K., van Eekelen, C. C., van der Korput, J. A., Brinkmann, A. O., and Trapman, J., Both androgen receptor and glucocorticoid receptor are able to induce prostate-specific antigen expression, but differ in their growth-stimulating properties of LNCaP cells, *Endocrinology*, 138(12):5293–300 (1997)

Colligan et al, *Current Protocols in Immunology*, Green Publishing Assoc., and Wiley Interscience, New York (2002)

Dorkin et al., "Basic science aspects of prostate cancer", *Semin Cancer Biol*, 8:21–7 (1997)

Eshhar et al, "Chimeric T cell receptor which incorporates the anti-tumour specificity of a monoclonal antibody with the cytolytic activity of T cells: a model system for immunotherapeutical approach", *Br J Cancer Suppl*, 10:27–29 (1990)

Fang et al., "Hsp90 regulates androgen receptor hormone binding affinity in vivo", *J Biol Chem*, 271:28697–702 (1996)

Fang et al., "SBA1 encodes a yeast hsp90 cochaperone that is homologous to vertebrate p23 proteins", *Mol Cell Biol*, 18:3727–34 (1998)

Fronsdal, K., Engedal, N., Slagsvold, T., and Saatcioglu, F., CREB binding protein is a coactivator for the androgen receptor and mediates cross-talk with AP-1, J Biol Chem 273(48):31853–9 (1998)

Fujimoto, N., Yeh, S., Kang, H. Y., Inui, S., Chang, H. C., Mizokami, A., and Chang, C., Cloning and characterization of androgen receptor coactivator, ARA55, in human prostate, *J Biol Chem*, 274(12):8316–21 (1999)

Gioeli, D., Ficarro, S. B., Kwiek, J. J., Aaronson, D., Hancock, M., Catling, A. D., White, F. M., Christian, R. E., Settlage, R. E., Shabanowitz, J., Hunt, D. F., and Weber, M. J., Androgen receptor phosphorylation. Regulation and identification of the phosphorylation sites, *J Biol Chem*, 277(32):29304–14 (2002)

Glass, C. K., and Rosenfeld, M. G., *Genes Dev* 14(2): 121–41 (2000)

Gross et al, "Expression of immunoglobulin-T-cell receptor chimeric molecules as functional receptors with antibody-type specificity", *Proc Natl Acad Sci USA*, 86:10024–10028 (1989)

Hakimi et al., "Androgen-receptor gene structure and function in prostate cancer", *World J Urol*, 14:329–37 (1996)

Harlow et al, Antibodies: A Laboratory Manual, Cold Spring Harbor Laboratory, Cold Spring Harbor, N.Y. (1988)

Heinlein, C. A., Ting, H. J., Yeh, S., and Chang, C., Identification of ARA70 as a ligand-enhanced coactivator for the peroxisome proliferator-activated receptor gamma, *J Biol Chem*, 274(23):16147–52 (1999)

Hsiao, P. W., and Chang, C., Isolation and characterization of ARA160 as the first androgen receptor N-terminal-associated coactivator in human prostate cells, *J Biol Chem*, 274(32):22373–9 (1999)

Jenster et al., "Domains of the human androgen receptor involved in steroid binding, transcriptional activation, and subcellular localization", *Mol Endocrinol*, 5:1396–404 (1991)

Jenster et al., "Functional domains of the human androgen receptor", *J Steroid Biochem Mol Biol*, 41:671–5 (1992)

Jenster, "The role of the androgen receptor in the development and progression of prostate cancer", *Semin Oncol*, 26:407–21 (1999)

Jenster, G., van der Korput, H. A., Trapman, J., and Brinkmann, A. O., Identification of two transcription activation units in the N-terminal domain of the human androgen receptor, *J Biol Chem* 270(13):7341–6 (1995)

Kang, H. Y., Yeh, S., Fujimoto, N., and Chang, C., *J Biol Chem*, 274(13):8570–6 (1999)

Kohler et al, "Continuous cultures of fused cells secreting antibody of predefined specificity", *Nature* 256:495–497 (1975)

Lee, K. A., Bindereif, A., and Green, M. R., *Gene Anal Tech*, 5(2):22–31 (1988)

Lin, H. K., Wang, L., Hu, Y. C., Altuwaijri, S., and Chang, C., *Embo J*, 21(15):4037–48 (2002)

Lin, H. K., Yeh, S., Kang, H. Y., and Chang, C., *Proc Natl Acad Sci USA*, 98(13):7200–5 (2001)

Liu et al, "Chimeric mouse-human IgG1 antibody that can mediate lysis of cancer cells" *Proc Natl Acad Sci USA* 84:3439–3443 (1987)

Lubahn, D. B., Joseph, D. R., Sar, M., Tan, J., Higgs, H. N., Larson, R. E., French, F. S. and Wilson, E. M., The human androgen receptor: complementary deoxyribonucleic acid cloning, sequence analysis and gene expression in prostate, *Mol. Endocrinol.*, 2(12):1265–1275 (1988)

Moilanen, A. M., Karvonen, U., Poukka, H., Janne, O. A., and Palvimo, J. J., Activation of androgen receptor function by a novel nuclear protein kinase, *Mol Biol Cell*, 9(9):2527–43 (1998)

Morrison et al, "Chimeric human antibody molecules: mouse antigen-binding domains with human constant region domains". *Proc Natl Acad Sci USA* 81:6851–6855 (1984)

Muller, J. M., Isele, U., Metzger, E., Rempel, A., Moser, M., Pscherer, A., Breyer, T., Holubarsch, C., Buettner, R., and Schule, R., *Embo J*, 19(3):359–69 (2000)

Nakatani, K., Thompson, D. A., Barthel, A., Sakaue, H., Liu, W., Weigel, R. J., and Roth, R. A., Up-regulation of Akt3 in estrogen receptor-deficient breast cancers and androgen-independent prostate cancer lines, *J Biol Chem*, 274 (31):21528–32 (1999)

Neuberger et al, "A hapten-specific chimaeric IgE antibody with human physiological effector function", *Nature* 314: 268–270 (1985)

Picard et al., "Reduced levels of hsp90 compromise steroid receptor action in vivo", *Nature*, 348:166–8 (1990)

Sahagan et al, "A genetically engineered murine/human chimeric antibody retains specificity for human tumor-associated antigen" *J Immunol*, 137:1066–1074 (1986)

Scheller, A., Hughes, E., Golden, K. L., and Robins, D. M., Multiple receptor domains interact to permit, or restrict, androgen-specific gene activation, *J Biol Chem*, 273(37), 24216–22 (1998)

Segnitz et al., "The function of steroid hormone receptors is inhibited by the hsp90-specific compound geldanamycin", *J Biol Chem*, 272:18694–701 (1997)

Suina et al., 1996

Sun et al, "Chimeric antibody with human constant regions and mouse variable regions directed against carcinoma-associated antigen 17–1A", *Proc Natl Acad Sci USA* 84:214–218 (1987)

Trapman et al., "The androgen receptor in prostate cancer", *Pathol Res Pract* 192:752–60 (1996)

Wen, Y., Hu, M. C., Makino, K., Spohn, B., Bartholomeusz, G., Yan, D. H., and Hung, M. C., *Cancer Res*, 60(24): 6841–5 (2000)

Westin, S., Rosenfeld, M. G., and Glass, C. K., Nuclear receptor coactivators, *Adv Pharmacol*, 47:89–112 (2000)

Wilson et al., "Molecular analysis of the androgen receptor", *Ann N Y Acad Sci*, 637:56–63 (1991)

Zhou, Z. X., Kemppainen, J. A., and Wilson, E. M., *Mol Endocrinol*, 9(5):605–15 (1995)

Zhu, Z., Becklin, R. R., Desiderio, D. M., and Dalton, J. T., *Biochem Biophys Res Commun*, 284(3):836–44 (2001)

SEQUENCE LISTING

```
<160> NUMBER OF SEQ ID NOS: 3

<210> SEQ ID NO 1
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: misc_feature
```

```
<222> LOCATION: (12)..(12)
<223> OTHER INFORMATION: Serine residue 12 is phosphorylated.

<400> SEQUENCE: 1

Glu Gly Ser Ser Ser Gly Arg Ala Arg Glu Ala Ser Gly Ala Pro Thr
1               5                   10                  15

Ser Ser

<210> SEQ ID NO 2
<211> LENGTH: 7
<212> TYPE: PRT
<213> ORGANISM: Artificial
<220> FEATURE:
<223> OTHER INFORMATION: synthetic

<400> SEQUENCE: 2

Arg Ala Arg Glu Ala Ser Gly
1               5

<210> SEQ ID NO 3
<211> LENGTH: 6
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Residue 6 is Ser or Thr.

<400> SEQUENCE: 3

Arg Xaa Arg Xaa Xaa Xaa
1               5
```

What is claimed is:

1. An isolated antibody or antigen-binding portion thereof specific for the human androgen receptor phosphorylated at the serine residue found at position 213 of SEQ ID NO:4 wherein the antibody or antigen-binding portion thereof binds to SEQ ID NO: 1.

2. The antibody or antigen-binding portion thereof of claim 1, wherein the antibody polyclonal antibody.

3. The antibody or antigen-binding portion thereof of claim 1, wherein the antibody monoclonal antibody.

* * * * *

UNITED STATES PATENT AND TRADEMARK OFFICE
CERTIFICATE OF CORRECTION

PATENT NO.         : 7,160,989 B2
APPLICATION NO.    : 10/849545
DATED              : January 9, 2007
INVENTOR(S)        : Logan et al.

It is certified that error appears in the above-identified patent and that said Letters Patent is hereby corrected as shown below:

At column 17, after the last line of the sequence listing, please insert the following:

--
<210> 4
<211> 919
<212> PRT
<213> Homo sapiens

<400> 4
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
            35                  40                  45

Pro Pro Gly Ala Ser Leu Leu Leu Leu Gln Gln Gln Gln Gln Gln Gln
            50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gln Gly Glu Asp Gly Ser Pro Gln
            85                  90                  95

Ala His Arg Arg Gly Pro Thr Gly Tyr Leu Val Leu Asp Glu Glu Gln
            100                 105                 110

UNITED STATES PATENT AND TRADEMARK OFFICE
CERTIFICATE OF CORRECTION

PATENT NO. : 7,160,989 B2
APPLICATION NO. : 10/849545
DATED : January 9, 2007
INVENTOR(S) : Logan et al.

It is certified that error appears in the above-identified patent and that said Letters Patent is hereby corrected as shown below:

```
Gln Pro Ser Gln Pro Gln Ser Ala Leu Glu Cys His Pro Glu Arg Gly
     115                 120                 125
Cys Val Pro Glu Pro Gly Ala Ala Val Ala Ala Ser Lys Gly Leu Pro
     130                 135                 140
Gln Gln Leu Pro Ala Pro Pro Asp Glu Asp Asp Ser Ala Ala Pro Ser
145                 150                 155                 160
Thr Leu Ser Leu Leu Gly Pro Thr Phe Pro Gly Leu Ser Ser Cys Ser
               165                 170                 175
Ala Asp Leu Lys Asp Ile Leu Ser Glu Ala Ser Thr Met Gln Leu Leu
         180                 185                 190
Gln Gln Gln Gln Gln Glu Ala Val Ser Glu Gly Ser Ser Ser Gly Arg
     195                 200                 205
Ala Arg Glu Ala Ser Gly Ala Pro Thr Ser Ser Lys Asp Asn Tyr Leu
    210                 215                 220
Gly Gly Thr Ser Thr Ile Ser Asp Asn Ala Lys Glu Leu Cys Lys Ala
225                 230                 235                 240
Val Ser Val Ser Met Gly Leu Gly Val Glu Ala Leu Glu His Leu Ser
                245                 250                 255
Pro Gly Glu Gln Leu Arg Gly Asp Cys Met Tyr Ala Pro Leu Leu Gly
             260                 265                 270
Val Pro Pro Ala Val Arg Pro Thr Pro Cys Ala Pro Leu Ala Glu Cys
           275                 280                 285
Lys Gly Ser Leu Leu Asp Asp Ser Ala Gly Lys Ser Thr Glu Asp Thr
       290                 295                 300
Ala Glu Tyr Ser Pro Phe Lys Gly Gly Tyr Thr Lys Gly Leu Glu Gly
 305                 310                 315                 320
Glu Ser Leu Gly Cys Ser Gly Ser Ala Ala Ala Gly Ser Ser Gly Thr
                325                 330                 335
Leu Glu Leu Pro Ser Thr Leu Ser Leu Tyr Lys Ser Gly Ala Leu Asp
             340                 345                 350
Glu Ala Ala Ala Tyr Gln Ser Arg Asp Tyr Tyr Asn Phe Pro Leu Ala
           355                 360                 365
Leu Ala Gly Pro Pro Pro Pro Pro Pro Pro His Pro His Ala Arg
       370                 375                 380
```

Page 2 of 6

UNITED STATES PATENT AND TRADEMARK OFFICE
CERTIFICATE OF CORRECTION

PATENT NO. : 7,160,989 B2
APPLICATION NO. : 10/849545
DATED : January 9, 2007
INVENTOR(S) : Logan et al.

It is certified that error appears in the above-identified patent and that said Letters Patent is hereby corrected as shown below:

```
Ile Lys Leu Glu Asn Pro Leu Asp Tyr Gly Ser Ala Trp Ala Ala Ala
385              390                 395                 400

Ala Ala Gln Cys Arg Tyr Gly Asp Leu Ala Ser Leu His Gly Ala Gly
          405                 410                 415

Ala Ala Gly Pro Gly Ser Gly Ser Pro Ser Ala Ala Ala Ser Ser Ser
           420                 425                 430

Trp His Thr Leu Phe Thr Ala Glu Glu Gly Gln Leu Tyr Gly Pro Cys
           435                 440                 445

Gly Gly Gly Gly Gly Gly Gly Gly Gly Gly Gly Gly Gly Gly Gly
      450                 455                 460

Gly Gly Gly Gly Gly Gly Gly Gly Glu Ala Gly Ala Val Ala Pro Tyr
465              470                 475                 480

Gly Tyr Thr Arg Pro Pro Gln Gly Leu Ala Gly Gln Glu Ser Asp Phe
           485                 490                 495

Thr Ala Pro Asp Val Trp Tyr Pro Gly Gly Met Val Ser Arg Val Pro
           500                 505                 510

Tyr Pro Ser Pro Thr Cys Val Lys Ser Glu Met Gly Pro Trp Met Asp
           515                 520                 525
```

UNITED STATES PATENT AND TRADEMARK OFFICE
CERTIFICATE OF CORRECTION

PATENT NO.       : 7,160,989 B2
APPLICATION NO.  : 10/849545
DATED            : January 9, 2007
INVENTOR(S)      : Logan et al.

It is certified that error appears in the above-identified patent and that said Letters Patent is hereby corrected as shown below:

```
Ser Tyr Ser Gly Pro Tyr Gly Asp Met Arg Leu Glu Thr Ala Arg Asp
    530             535             540

His Val Leu Pro Ile Asp Tyr Tyr Phe Pro Pro Gln Lys Thr Cys Leu
545             550             555             560

Ile Cys Gly Asp Glu Ala Ser Gly Cys His Tyr Gly Ala Leu Thr Cys
            565             570             575

Gly Ser Cys Lys Val Phe Phe Lys Arg Ala Ala Glu Gly Lys Gln Lys
        580             585             590

Tyr Leu Cys Ala Ser Arg Asn Asp Cys Thr Ile Asp Lys Phe Arg Arg
        595             600             605

Lys Asn Cys Pro Ser Cys Arg Leu Arg Lys Cys Tyr Glu Ala Gly Met
    610             615             620

Thr Leu Gly Ala Arg Lys Leu Lys Lys Leu Gly Asn Leu Lys Leu Gln
625             630             635             640

Glu Glu Gly Glu Ala Ser Ser Thr Thr Ser Pro Thr Glu Glu Thr Thr
            645             650             655

Gln Lys Leu Thr Val Ser His Ile Glu Gly Tyr Glu Cys Gln Pro Ile
            660             665             670
```

UNITED STATES PATENT AND TRADEMARK OFFICE
CERTIFICATE OF CORRECTION

PATENT NO. : 7,160,989 B2
APPLICATION NO. : 10/849545
DATED : January 9, 2007
INVENTOR(S) : Logan et al.

It is certified that error appears in the above-identified patent and that said Letters Patent is hereby corrected as shown below:

Phe Leu Asn Val Leu Glu Ala Ile Glu Pro Gly Val Val Cys Ala Gly
          675                680              685

His Asp Asn Asn Gln Pro Asp Ser Phe Ala Ala Leu Leu Ser Ser Leu
          690                695              700

Asn Glu Leu Gly Glu Arg Gln Leu Val His Val Val Lys Trp Ala Lys
    705                710              715              720

Ala Leu Pro Gly Phe Arg Asn Leu His Val Asp Asp Gln Met Ala Val
              725                730              735

Ile Gln Tyr Ser Trp Met Gly Leu Met Val Phe Ala Met Gly Trp Arg
          740                745              750

Ser Phe Thr Asn Val Asn Ser Arg Met Leu Tyr Phe Ala Pro Asp Leu
          755                760              765

Val Phe Asn Glu Tyr Arg Met His Lys Ser Arg Met Tyr Ser Gln Cys
          770                775              780

Val Arg Met Arg His Leu Ser Gln Glu Phe Gly Trp Leu Gln Ile Thr
    785                790              795              800

Pro Gln Glu Phe Leu Cys Met Lys Ala Leu Leu Leu Phe Ser Ile Ile
              805                810              815

Pro Val Asp Gly Leu Lys Asn Gln Lys Phe Phe Asp Glu Leu Arg Met
              820                825              830

Asn Tyr Ile Lys Glu Leu Asp Arg Ile Ile Ala Cys Lys Arg Lys Asn
              835                840              845

Pro Thr Ser Cys Ser Arg Arg Phe Tyr Gln Leu Thr Lys Leu Leu Asp
              850                855              860

Ser Val Gln Pro Ile Ala Arg Glu Leu His Gln Phe Thr Phe Asp Leu
    865                870              875              880

Leu Ile Lys Ser His Met Val Ser Val Asp Phe Pro Glu Met Met Ala
              885                890              895

Glu Ile Ile Ser Val Gln Val Pro Lys Ile Leu Ser Gly Lys Val Lys
              900                905              910

Pro Ile Tyr Phe His Thr Gln
          915

UNITED STATES PATENT AND TRADEMARK OFFICE
CERTIFICATE OF CORRECTION

PATENT NO. : 7,160,989 B2
APPLICATION NO. : 10/849545
DATED : January 9, 2007
INVENTOR(S) : Logan et al.

It is certified that error appears in the above-identified patent and that said Letters Patent is hereby corrected as shown below:

In claim 2, column 18, line 45, after the first occurrence of the word "antibody", please insert --is a--.
In claim 3, column 18, line 47, after the first occurrence of the word "antibody", please insert --is a--.

Signed and Sealed this

Twenty-second Day of December, 2009

David J. Kappos
*Director of the United States Patent and Trademark Office*